United States Patent
Albrecht et al.

(10) Patent No.: US 9,869,679 B2
(45) Date of Patent: Jan. 16, 2018

(54) METHODS AND DEVICES FOR PHOTOMETRICALLY DETERMINING SAMPLE APPLICATION ON TEST ELEMENTS

(71) Applicant: Roche Diabetes Care, Inc., Indianapolis, IN (US)

(72) Inventors: Gertrud Albrecht, Mannheim (DE); Otto Gaa, Worms (DE); Robert Lorenz, Worms (DE); Frank Rueckert, Ludwigshafen (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 209 days.

(21) Appl. No.: 14/639,602

(22) Filed: Mar. 5, 2015

(65) Prior Publication Data
US 2015/0177257 A1    Jun. 25, 2015

Related U.S. Application Data (63) Continuation of application No. PCT/EP2013/068401, filed on Sep. 5, 2013.

(30) Foreign Application Priority Data

Sep. 5, 2012 (EP) .................................. 12183225

(51) Int. Cl.
*G01N 33/66* (2006.01)
*G01N 33/50* (2006.01)
*G01N 21/84* (2006.01)

(52) U.S. Cl.
CPC ......... *G01N 33/66* (2013.01); *G01N 21/8483* (2013.01); *Y10T 436/144444* (2015.01)

(58) Field of Classification Search
CPC ........ G01N 33/66; G01N 33/50; G01N 33/48; G01N 21/8483; G01N 21/84; B01J 19/0046; B01J 19/00
(Continued)

(56) References Cited

U.S. PATENT DOCUMENTS 6,055,060 A * 4/2000 Bolduan ............ G01N 21/8483
                                                            356/39
6,458,596 B1   10/2002 Poellmann
(Continued)

FOREIGN PATENT DOCUMENTS

DE    19932846 A1   1/2001
EP     2221608 A1   2/2009
(Continued)

OTHER PUBLICATIONS

English Machine Tranlation of EP 2 221 608 A1, obtained on Nov. 23, 2016, pp. 1-28.*

*Primary Examiner* — Christine T Mui
(74) *Attorney, Agent, or Firm* — Stinson Leonard Street LLP (57) ABSTRACT

Methods are provided for photometrically determining/detecting sample application to an analytical test element for use with a blood glucose measuring device, where the method includes obtaining a sequence of reflectance readings from the test element with the measuring device, including a blank value prior to sample application, and then monitoring changes of the reflectance readings from the test element with respect to a sample application condition defined by a limit for a reflectance decrease or a reflectance threshold. The methods also can include adjusting the sample application condition in accordance with a drift correction and can include determining an analyte concentration in the body fluid sample. In addition, photometric (Continued)

blood glucose measuring devices are provided that incorporate the methods disclosed herein.

15 Claims, 4 Drawing Sheets

(58) Field of Classification Search
USPC ...... 436/95, 94, 93, 91; 422/82.05, 68.1, 50; 702/19, 1
See application file for complete search history.

(56) References Cited

U.S. PATENT DOCUMENTS

| | | | |
|---|---|---|---|
| 7,477,404 B2* | 1/2009 | Schulat | G01N 21/8483 356/39 |
| 9,052,293 B2* | 6/2015 | Miltner | G01N 21/8483 |
| 2012/0010489 A1 | 1/2012 | Miltner et al. | |

FOREIGN PATENT DOCUMENTS

| | | |
|---|---|---|
| WO | 01/19187 A1 | 3/2001 |
| WO | 01/25760 A1 | 4/2001 |

* cited by examiner

METHODS AND DEVICES FOR PHOTOMETRICALLY DETERMINING SAMPLE APPLICATION ON TEST ELEMENTS

CROSS-REFERENCE TO RELATED APPLICATIONS

This patent application is a continuation of Intl Patent Application No. PCT/EP2013/068401 (filed 5 Sep. 2013), which claims priority to and the benefit of EP Patent Application No. 12183225.7 (filed 5 Sep. 2012). Each patent application is incorporated herein by reference as if set forth in its entirety.

TECHNICAL FIELD

This patent application relates generally to chemistry and medicine/medical diagnostics, and more particularly, it relates to methods of photometrically determining/detecting body fluid sample application to test elements based upon a sequence of reflectance readings that starts with a blank reading and monitoring such reflectance readings for a change with respect to at least one sample application condition, as well as measuring devices that incorporate such methods.

BACKGROUND

EP Patent Application Publication No. 2 221 608 discloses a test method and test device for analyzing a body fluid by means of analytical test fields stored on a test tape. To ensure an increased security against operating and measuring errors, a control value is determined from a time-dependent and/or wavelength-dependent change of the measurement signals. The measurement signals then are processed as valid or discarded as erroneous depending on a preset threshold value of the control value. This document further discloses that high air humidity, as well as exposure to UV radiation, may lead to a signal change similar to sample application, and thus result in a start of the measurement. In this context, it is proposed that body fluid/liquid sample application is detected when a signal change is above a predetermined threshold value (e.g., of about 5%), and a fault is detected when it is below this value if necessary after a specified waiting time. In the latter case, the test field is discarded, and the measurement must be repeated.

For the foregoing reasons, there is a need for improved methods of determining/detecting body fluid sample application to test elements to provide reliable results and to avoid a loss of test elements even under unfavorable ambient measurement conditions.

BRIEF SUMMARY

An inventive concept described herein includes providing a correction for slow signal drift in a test element without aborting sample recognition, where the signal drift can be caused by unfavorable ambient measurement conditions or environmental factors such as humidity, temperature and UV radiation. This inventive concept is achieved by adjusting a sample application condition in accordance with a drift correction calculated from a drift of the reflectance readings prior to sample application. The sample application condition is defined by a limit for a reflectance decrease or a reflectance threshold. The change of the reflectance readings can be monitored in a sample recognition cycle, where a value for drift correction can be provided to adjust the sample application condition without aborting the sample recognition cycle. In this manner, it is possible to avoid a loss of a test element as a consequence of an error detection. The test element remains usable, and the measuring procedure can be finished without additional delay. This inventive concept can be incorporated into exemplary methods and devices as described herein and in more detail below.

For example, methods of determining/detecting sample application can begin by providing a test element having a body fluid sample application area including a reagent composition for photometrically (or optically) detecting at least one analyte of interest in a body fluid sample. In some instances, the analyte of interest is glucose, especially blood glucose, and the body fluid sample is a blood sample.

The methods also can include obtaining a sequence of reflectance readings from the test element with a photometric blood glucose measuring device, where the sequence of reflectance readings starts with a blank reading.

The methods also can include monitoring changes in the sequence of reflectance readings in a sample recognition cycle with respect to a sample application condition to determine if the body fluid sample has been applied to the test element.

The methods also can include adjusting the sample application condition with a drift correction calculated from reflectance readings prior to applying the body fluid sample, where the sample application condition is defined by a limit for a reflectance decrease or a reflectance threshold, and where a value for the drift correction is provided to adjust the sample application condition without aborting the sample recognition cycle. The drift of the reflectance readings can be caused by ambient measurement conditions such as humidity, temperature and UV radiation.

In some instances, the sample application condition is fulfilled when a difference between the blank reading and an actual reflectance reading in the sequence of reflectance readings is higher than a given reflectance decrease, and the value for the drift correction is added to a predefined signal decrease to obtain the given reflectance decrease.

In other instances, the sample application condition is fulfilled when an actual reflectance reading in the sequence of reflectance readings is less than a given reflectance threshold, and the value for the drift correction is subtracted from a predefined signal threshold to obtain the given reflectance threshold.

The methods also can include confirming sample application by a further reflectance reading after fulfilling the sample application condition.

Moreover, the methods can include calculating the value for the drift correction from the blank reading and one or more reflectance readings taken before the sample application condition is fulfilled.

Likewise, the methods can include determining an analyte concentration in the sample using at least one reflectance reading after the sample application condition is fulfilled.

Furthermore, the methods can include defining a limit for the value for the drift correction and terminating the method if the limit is exceeded.

In view of the foregoing, the photometric measuring devices can include a receiving unit configured to receive a test element on which a body fluid sample can be applied. In addition, the devices can include a photometric detector configured to take a sequence of reflectance readings from the test element, where the sequence of reflectance readings starts with a blank reading. Moreover, the devices include a signal processor configured to monitor a change of reflectance readings in a sample recognition cycle with respect to a sample application condition to determine if the body fluid sample has been applied to the test element. Furthermore, the devices include an arithmetic unit configured to calculate a drift correction from reflectance readings prior to body fluid sample application and to adjust the sample application condition in accordance with the drift correction, where the sample application condition is defined by a limit for a reflectance decrease or a reflectance threshold, and where a value for the drift correction is provided for adjusting the sample application condition without aborting the sample recognition cycle and further to confirm the body fluid sample by a further reflectance reading after fulfilling the sample application condition.

The methods and devices described herein therefore find use in monitoring the presence or concentration of an analyte of interest in a body fluid sample, especially a medically significant analyte such as glucose.

These and other advantages, effects, features and objects of the inventive concept will become better understood from the description that follows. In the description, reference is made to the accompanying drawings, which form a part hereof and in which there is shown by way of illustration, not limitation, embodiments of the inventive concept.

BRIEF DESCRIPTION OF THE DRAWINGS

The advantages, effects, features and objects other than those set forth above will become more readily apparent when consideration is given to the detailed description below. Such detailed description makes reference to the following drawings, wherein.

Corresponding reference characters indicate corresponding parts throughout the several views of the drawings.

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, features and objects falling within the spirit and scope thereof as defined by the embodiments described herein and the claims below. Reference should therefore be made to the embodiments described herein and claims below for interpreting the scope of the inventive concept. As such, it should be noted that the embodiments described herein may have advantages, effects, features and objects useful in solving other problems.

DESCRIPTION OF EXEMPLARY EMBODIMENTS

The methods and devices now will be described more fully hereinafter with reference to the accompanying drawings, in which some, but not all embodiments of the inventive concept are shown. Indeed, the methods and devices may be embodied in many different forms and should not be construed as limited to the embodiments set forth herein; rather, these embodiments are provided so that this disclosure will satisfy applicable legal requirements.

Likewise, many modifications and other embodiments of the methods and devices described herein will come to mind to one of skill in the art to which the disclosure pertains having the benefit of the teachings presented in the foregoing descriptions and the associated drawings. Therefore, it is to be understood that the methods and devices are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the methods and devices, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one." Likewise, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. For example, the expressions "A has B," "A comprises B" and "A includes B" may refer both to a situation in which, besides B, no other element is present in A (i.e., a situation in which A solely and exclusively consists of B) or to a situation in which, besides B, one or more further elements are present in A, such as element C, elements C and D, or even further elements.

Overview

Test elements used in connection with body fluid analysis for an analyte of interest, such as blood glucose, tend to be sensitive to the environment, as well as to ambient measurement conditions. For example, humidity, temperature and UV radiation can cause deterioration in the reagent materials of such test elements and thus negatively affect test element performance, including whether sample application has occurred. As such, there is a need for improved methods of determining/detecting sample application to test elements to thereby provide reliable results and to avoid a loss of test elements even under unfavorable ambient measurement conditions. An inventive concept described herein includes providing a correction for slow signal drift without aborting sample recognition. This inventive concept is achieved by adjusting a sample application condition in accordance with a drift correction calculated from a drift of the reflectance readings prior to sample application.

Figure 1:
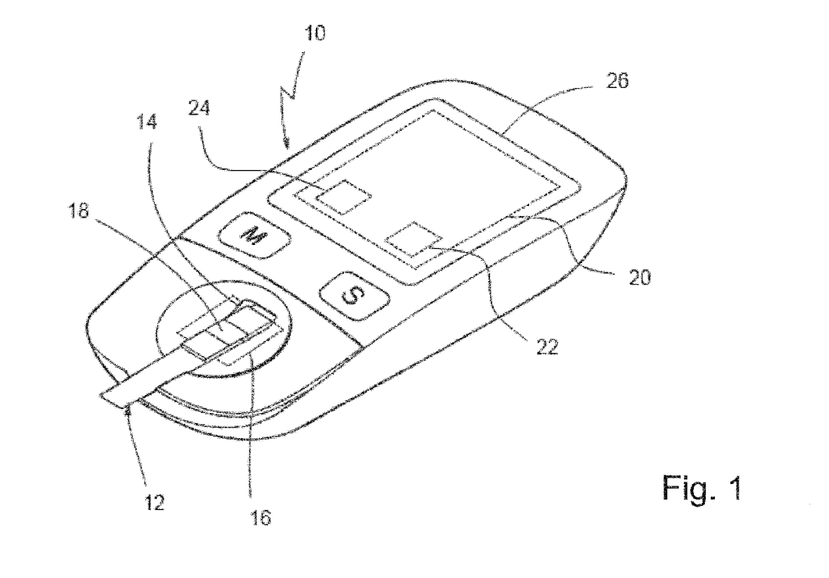
FIG. 1 shows a partial schematic perspective view of a glucose meter with a test element inserted for a body fluid sample (e.g., blood) application.

FIG. 1 schematically illustrates a photometric reflectance measuring device designed as a handheld blood glucose meter 10 that can receive a disposable test strip 12. The meter 10 includes a test strip holder or strip grip 14 to position the test strip 12 in the optical path of a reflection photometer 16 as a detector to read the reflectance of an analytical test pad 18 of the test strip 12 at a plurality of time points. A small volume of body fluid sample can be applied to the upper surface of the test pad 18, where a reagent reacts with an analyte of interest, such as glucose, thereby leading to a change in reflectance. Such reflectance changes can be detected from the bottom of the test pad 18 with the photometer 16, which includes a light source and a light sensor arranged in a reflection path for diffuse reflection or remission of light (not shown). Then, the reflectance (remission) changes over a predetermined time period as a result of formation of reaction product can be related to the amount of analyte in the sample. Such measurements are known to one of skill in the art. See, e.g., DE Patent Application Publication No. 199 32 846, and thus need not to be elucidated in further detail herein.

To process the measurement signals or reflectance readings, a device electronics 20 includes a signal processor 22 in combination with an arithmetic unit 24, which provides a measurement result on a display 26 directly to the user. The signal processor 22 allows amplification and A/D conversion of the reflectance readings, and the arithmetic unit 24 enables further data handling specifically with respect to a drift correction, as explained below.

Figure 2:
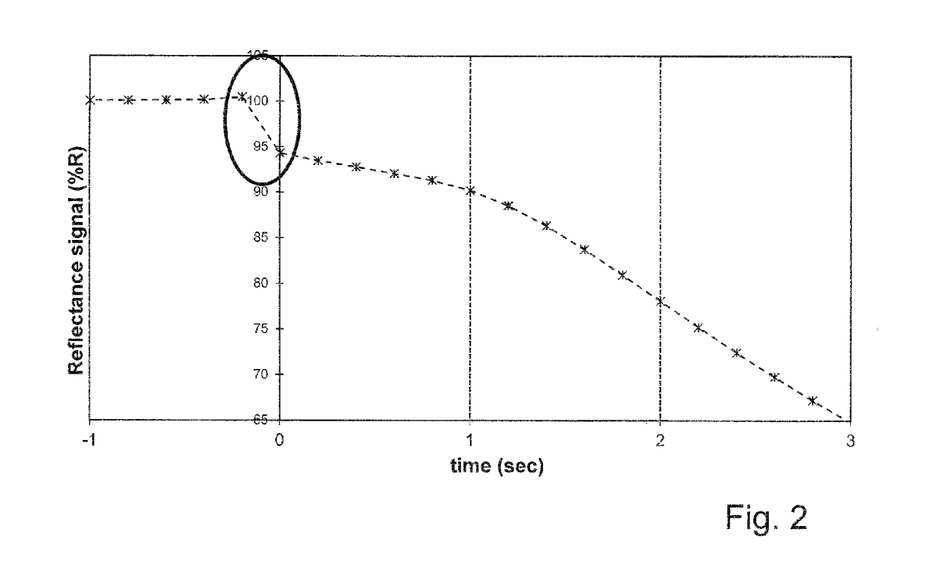
FIG. 2 shows a time diagram of a sequence of reflectance readings taken from the test element before and after sample application.

FIG. 2 illustrates a characteristic time course of reflectance readings that can be obtained using the meter of FIG. 1, where a time period in which the sample is applied is highlighted by an ellipse. The diagram shows relative reflectance readings/remission values taken at constant intervals over the time and normalized to 100%. In a first phase, before the body fluid sample is applied, the reflectance of the yet unused test pad 14 remains essentially constant under normal conditions. Upon sample application, a sudden decrease in the remission behavior occurs due to the dry-wet transition of the test pad 18. This significant decrease can be used to automatically recognize sample application and to set the time zero point for the reaction kinetics of the reagent with the analyte. Subsequently, the remission gradually begins lowering until the monitoring of the kinetics is terminated. Then, the analyte (e.g., glucose) concentration can be determined from the kinetics by calculating a quotient from an end and starting remission value.

Figure 3:
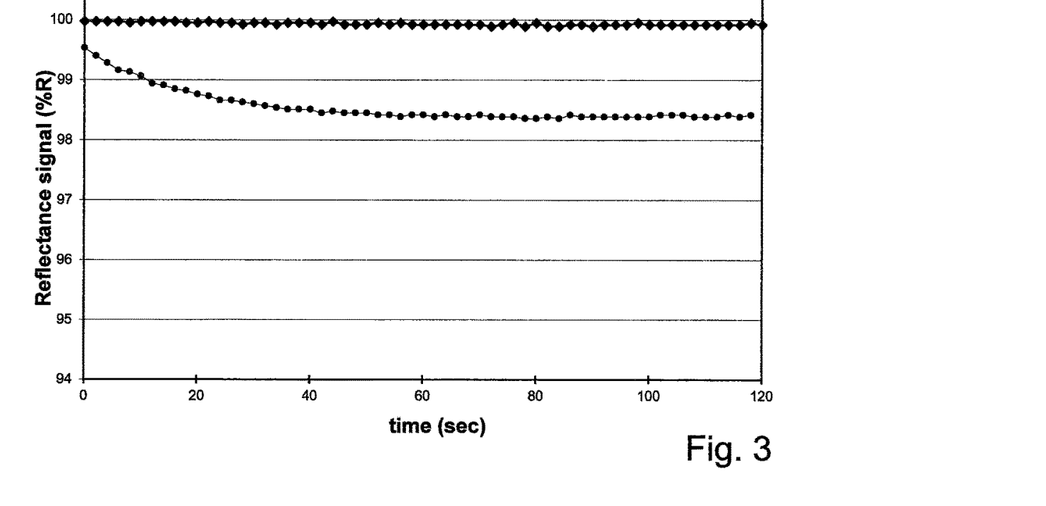
FIG. 3 shows a time diagram of reflectance readings illustrating a signal drift due to air humidity.

Turning now to FIG. 3, the time course of the reflectance or remission of an unused test strip 12 is illustrated for different ambient conditions. The diamonds indicate measurements at relatively low air humidity with no significant change, whereas the circles indicate measurements at high humidity resulting in a slow signal drift as compared to the fast dry-wet transition mentioned above. Nevertheless, if the deviation of such a slow drift is falsely interpreted as a sample application by the meter, a measurement cycle could be started leading to a gross wrong result. A signal drift before sample application also can be caused by other unfavorable boundary conditions, including exposure to strong UV radiation.

The inventive concept provides the following advantages with respect to the methods and devices disclosed herein:

For example, the sample application condition is automatically regarded as fulfilled when a difference between the blank reading and an actual reflectance reading in the sequence of reflectance readings is higher than a given reflectance decrease. In this case, it is automatically determined that sample has been applied. Such a given reflectance decrease can be advantageously obtained by adding a value for drift correction to a predefined signal decrease.

Likewise, the sample application condition is automatically regarded as fulfilled when an actual reflectance reading in the sequence of reflectance readings is less than a given reflectance threshold. Then, it is automatically determined that sample has been applied. Such a given reflectance threshold can be advantageously determined by subtracting a value for drift correction from a predefined signal threshold.

Another advantage is that a value for drift correction is calculated from the blank reading and one or more last or most recent reflectance readings taken before the sample application condition is fulfilled.

To average small short-time deviations, a mean actual reflectance can be calculated as a mean value from a given number of last reflectance readings and can be subtracted from the blank reading to obtain a value for drift correction.

For further improvement of the measurement certainty, it is advantageous when sample application is confirmed by a further reflectance reading after fulfillment of the sample application condition.

It is also advantageous for a further automatic processing when the analyte concentration in the sample is determined using at least one reflectance reading after fulfilling the sample application condition.

To avoid extreme conditions, it is advantageous when defining a limit for the drift correction and terminating the measurement if the limit is exceeded.

The proposed drift correction is particularly effective when a drift of the reflectance readings is caused by unfavorable ambient measurement conditions, such as humidity or temperature or UV radiation.

For a reliable discrimination it is favorable when upon sample application that a drop in reflectance of the test element occurs significantly faster than a drift of the reflectance readings.

With regard to a photometric measuring device adapted for determining sample application on an analytical test element specifically for glucose measurements measurement system, to solve the aforementioned object, it is proposed that an arithmetic unit is adapted or configured to calculate a drift correction from the reflectance readings prior to sample application and then to adjust the sample application condition in accordance with the drift correction.

Methods and Devices

Methods of the inventive concept include photometrically determining/detecting body fluid sample application on an analytical test element for use with a blood glucose measuring device. The methods can include the steps described herein, and these steps may be, but not necessarily, carried out in the sequence as described. Other sequences, however, also are conceivable. Furthermore, individual or multiple steps may be carried out either in parallel and/or overlapping in time and/or individually or in multiply repeated steps. Moreover, the methods may include additional, unspecified steps.

In general, the methods can begin by providing a test element having a body fluid sample application that includes a reagent composition for photometrically (or optically) detecting at least one analyte of interest in a body fluid sample. Such test elements are well known in the art and need not be exhaustively described herein. In some instances, the analyte of interest is glucose, especially blood glucose, and the body fluid sample is blood or a component thereof.

The methods also can include applying the body fluid sample to the test element. The body fluid sample can be obtained by any method as is known in the art, such as, for example, a lancing or piercing of the skin.

Once the body fluid sample is applied to the test element, a sequence of reflectance readings can be obtained from the test element with a photometric blood glucose measuring device as described above and in more detail below. Regardless, the sequence of reflectance readings starts with a blank reading.

Figure 4:
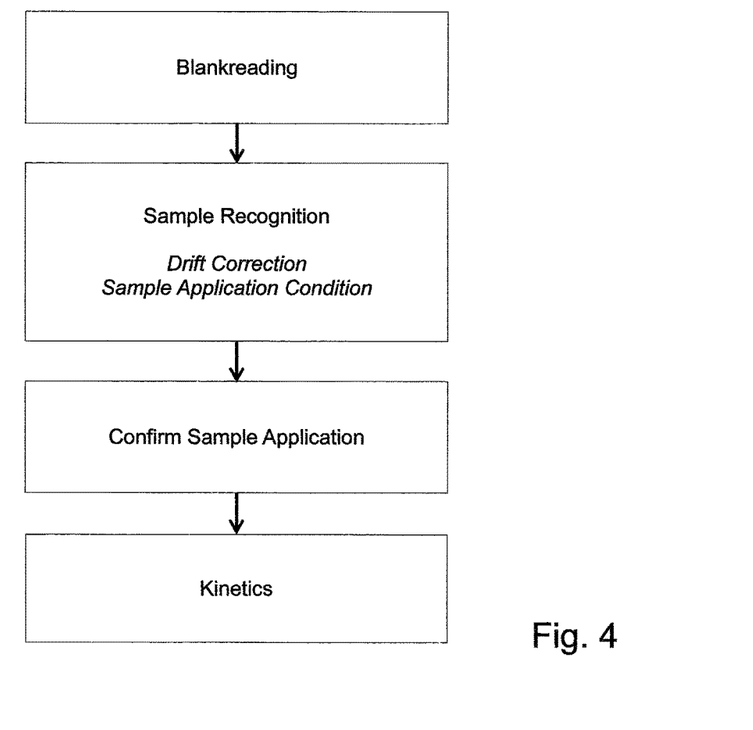
FIG. 4 shows a schematic diagram illustrating a method of operating a glucose meter.

FIG. 4 shows a simplified function scheme useful in understanding the inventive concept. After providing the test strip 12, but before sample application, a first reflectance reading on a dry test pad 18 of the test strip 12 is recorded by the measuring device as blankreading. Thereafter, a sample recognition cycle is started in which a change of the intermittently recorded reflectance readings is monitored by the measuring device with respect to a sample application condition, which can either be defined by a given reflectance decrease or reflectance threshold. Included in this recognition cycle is a drift correction routine to compensate for eventual deviation due to a slow signal drift. If the sample application condition is fulfilled, the actual sample application is again confirmed, and thereafter the reaction kinetics are recorded to obtain a valid measurement result (i.e., concentration) of the analyte of interest.

Figure 5:
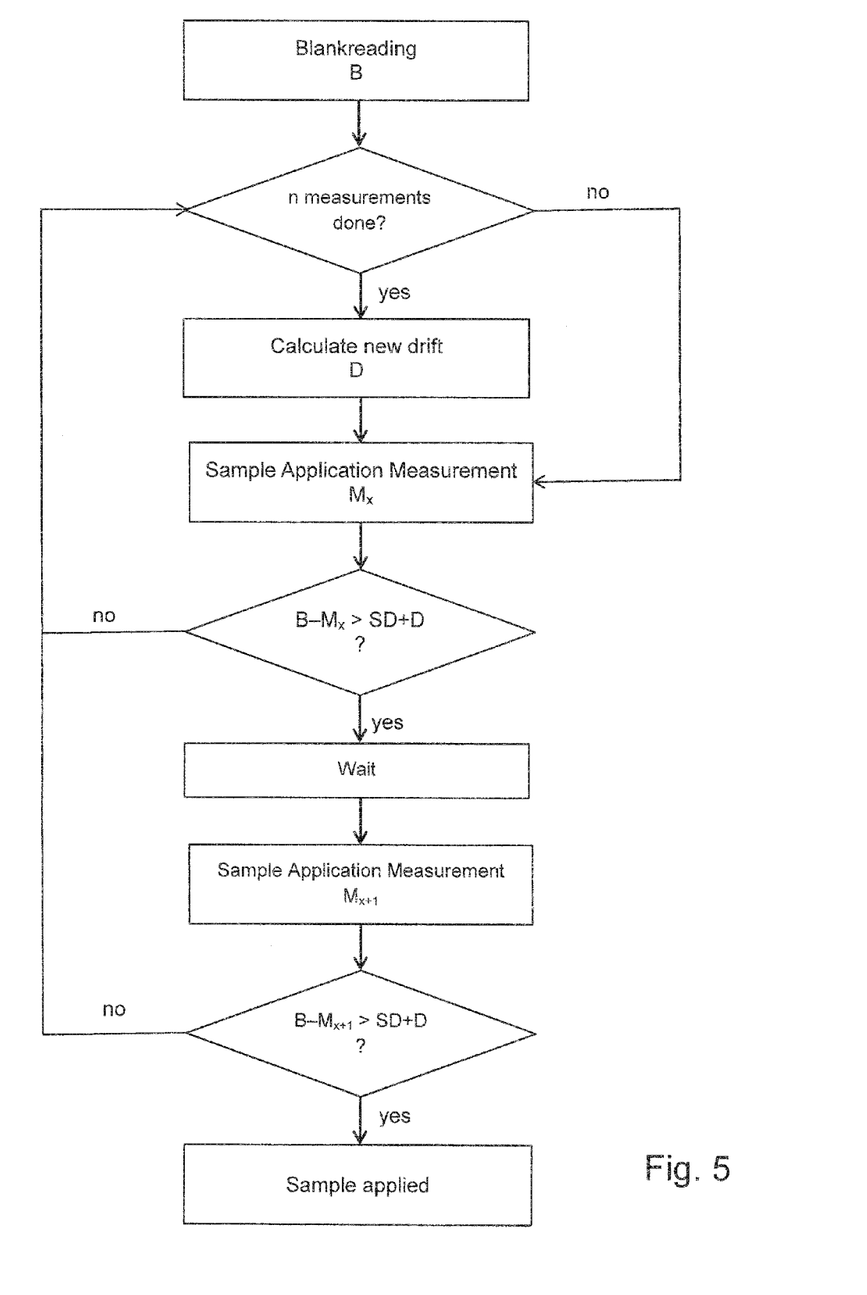
FIGS. 5 and 6 are flowcharts that show different exemplary methods of determining sample application on the test element in the meter of FIG. 1.

FIG. 5 provides a more detailed flowchart of a first exemplary method of photometrically determining/detecting sample application. Initially, a blankreading value B is determined as a first reflectance reading on the dry test strip 12. At the time of initialization, a value D for drift correction and a number n of measurements used therefor is set to zero.

As a next step, the sample recognition cycle is started. A new drift value D is calculated if a sufficient number n≥1 of further reflectance readings designated as sample application measurements $M_x$ are available after the blankreading. For example, the three latest measurements (n=3) may be taken to determine a mean reflectance value that is continuously recalculated in the sequence of further reflectance readings. The drift value D may be determined according to the following equation (1):

$$D = B - \left( \sum_{x}^{x-n+1} M_X \right) / n. \quad (1)$$

Accordingly, the drift value D is the difference between the initial blankreading and the mean reflectance value of a number of most recent reflectance readings.

In FIG. 5, an actual sample application measurement $M_x$ is monitored with respect to a sample application condition, which is in turn adjusted to account for an eventual drift. In this example, the sample application condition is fulfilled when a difference between the blankreading B and the actual reading $M_x$ is higher than a given reflectance decrease (i.e., higher than the sum of a predefined signal decrease SD and the drift D). The predefined signal decrease may be set according to the signal drop observed for the dry-wet transition as marked in FIG. 2 (e.g., to 5%).

If the sample application condition is fulfilled, a confirmation step is executed, in which after a defined waiting time the sample application measurement is repeated and the sample application condition is again controlled. In case of positive confirmation of the sample application, the recording of the reaction kinetics can be started to determine an analyte concentration.

Figure 6:
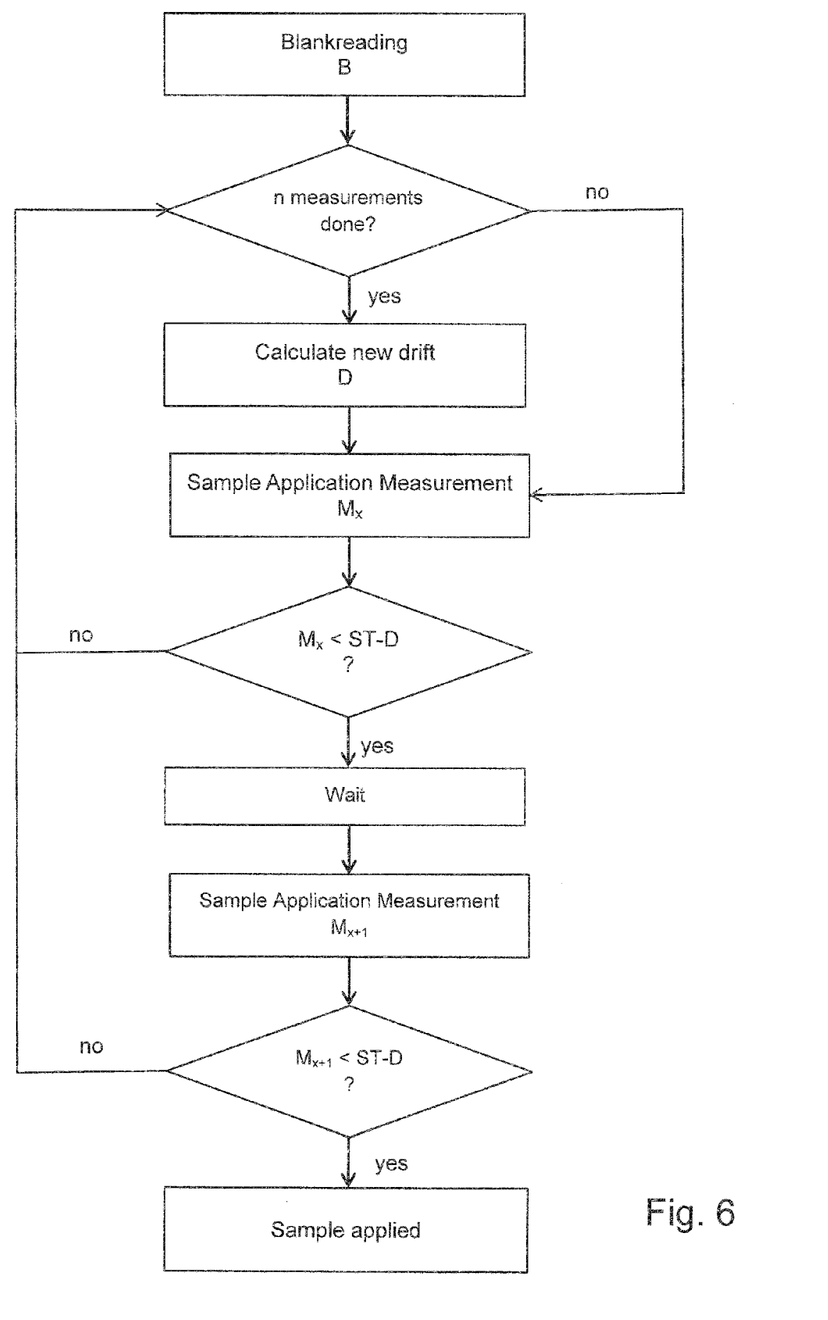

FIG. 6 shows an alternative exemplary method that only differs in the definition of the sample application condition. Here, a given reflectance threshold is controlled instead of monitoring a signal decrease. The given reflectance threshold is determined as the difference of an initial signal threshold ST (e.g., 95% of remission) and the drift D. The sample application condition fulfilled when the actual reflectance reading $M_x$ is less than said difference ST-D.

All of the patents, patent applications, patent application publications and other publications recited herein are hereby incorporated by reference as if set forth in their entirety.

The present inventive concept has been described in connection with what are presently considered to be the most practical and preferred embodiments. However, the inventive concept has been presented by way of illustration and is not intended to be limited to the disclosed embodiments. Accordingly, one of skill in the art will realize that the inventive concept is intended to encompass all modifications and alternative arrangements within the spirit and scope of the inventive concept as set forth in the appended claims.

The invention claimed is:

1. A method of photometrically determining whether a body fluid sample has been applied to an analytical test element, the method comprising the steps of:
    obtaining a sequence of reflectance readings from the analytical test element with a photometric blood glucose measuring device, wherein the sequence of reflectance readings starts with a blank reading;
    monitoring changes in the sequence of reflectance readings in a sample recognition cycle with respect to a sample application condition;
    adjusting the sample application condition with a drift correction calculated from the sequence of reflectance readings including the blank reading, wherein the sample application condition is defined by a limit for a reflectance decrease or a reflectance threshold, wherein a value for the drift correction is provided to adjust the sample application condition without aborting the sample recognition cycle;
    determining whether the sequence of reflectance readings fulfills the adjusted sample application condition; and
    on condition that the adjusted sample application condition is fulfilled, confirming that the body fluid sample has been applied to the analytical test element.

2. The method of claim 1, wherein the adjusted sample application condition is fulfilled when a difference between the blank reading and an actual reflectance reading in the sequence of reflectance readings is higher than a given reflectance decrease.

3. The method of claim 2, wherein the value for the drift correction is added to a predefined signal decrease to obtain the given reflectance decrease.

4. The method of claim 1, wherein the adjusted sample application condition is fulfilled when an actual reflectance reading in the sequence of reflectance readings is less than a given reflectance threshold.

5. The method of claim 4, wherein the value for the drift correction is subtracted from a predefined signal threshold to obtain the given reflectance threshold.

6. The method of claim 1 further comprising the step of calculating the value for the drift correction from the blank reading and one or more actual reflectance readings in the sequence of reflectance readings before the adjusted sample application condition is fulfilled.

7. The method of claim 1, wherein a mean actual reflectance is calculated as a mean value from a predetermined number of last reflectance readings in the sequence of reflectance readings and is subtracted from a blankreading value for the blank reading to obtain the value for the drift correction.

8. The method of claim 1 further comprising the step of determining an analyte concentration in the body fluid sample using at least one reflectance reading in the sequence of reflectance readings after the adjusted sample application condition is fulfilled.

9. The method of claim 1 further comprising the step of defining a limit for the value for the drift correction and terminating the method if the limit is exceeded.

10. The method of claim 1, wherein a drift of the reflectance readings in the sequence of reflectance readings is caused by ambient measurement conditions selected from the group consisting of humidity, temperature and UV radiation.

11. The method of claim 1, wherein the adjusted sample application condition is fulfilled when a drop in reflectance of the analytical test element occurs faster than a drift of the sequence of reflectance readings.

12. A blood glucose measuring device that photometrically determines whether a body fluid sample has been applied to an analytical test element, the device comprising:
a receiving unit configured to receive the analytical test element;
a photometric detector configured to take a sequence of reflectance readings from the analytical test element, wherein the sequence of reflectance readings starts with a blank reading;
a signal processor configured to monitor a change in the sequence of reflectance readings in a sample recognition cycle with respect to a sample application condition;
an arithmetic unit configured to calculate a drift correction from the sequence of reflectance readings and to adjust the sample application condition in accordance with the drift correction, wherein the sample application condition is defined by a limit for a reflectance decrease or a reflectance threshold, and wherein a value for the drift correction is provided for adjusting the sample application condition without aborting the sample recognition cycle and further for confirming the body fluid sample has been applied to the analytical test element before an analyte measurement is started by a further reflectance reading after the adjusted sample application condition is fulfilled.

13. The blood glucose measuring device of claim 12, wherein the analytical test element comprises a reagent configured to react with an analyte in the body fluid sample application and alter a reflectance of a test field of the analytical test element.

14. The blood glucose measuring device of claim 12, wherein the analytical test element is a disposable test strip, and the receiving unit is formed as a strip grip to position the analytical test strip with respect to the photometric detector.

15. The method of claim 1, wherein the drift correction is calculated after the sequence of reflectance readings includes a predetermined quantity of actual reflectance readings.

* * * * *